(12) United States Patent
Van Soest et al.

(10) Patent No.: US 12,226,185 B2
(45) Date of Patent: Feb. 18, 2025

(54) INTRAVASCULAR PHOTOACOUSTIC IMAGING

(71) Applicant: Erasmus University Medical Center Rotterdam, Rotterdam (NL)

(72) Inventors: Gijs Van Soest, Moordrecht (NL); Verya Daeichin, Rotterdam (NL); Antonius Franciscus Wilhelmus Van Der Steen, Rotterdam (NL)

(73) Assignee: Erasmus University Medical Center Rotterdam, Rotterdam (NL)

( * ) Notice: Subject to any disclaimer, the term of this patent is extended or adjusted under 35 U.S.C. 154(b) by 0 days.

(21) Appl. No.: 18/489,637

(22) Filed: Oct. 18, 2023

(65) Prior Publication Data

US 2024/0065551 A1   Feb. 29, 2024

Related U.S. Application Data

(63) Continuation of application No. 15/549,552, filed as application No. PCT/EP2016/052639 on Feb. 8, 2016, now Pat. No. 11,793,405.

(30) Foreign Application Priority Data

Feb. 9, 2015   (GB) ..................... 1502101

(51) Int. Cl.
*A61B 5/00*   (2006.01)
*A61B 5/02*   (2006.01)
(Continued)

(52) U.S. Cl.
CPC .......... *A61B 5/0035* (2013.01); *A61B 5/0044* (2013.01); *A61B 5/0086* (2013.01);
(Continued)

(58) Field of Classification Search
CPC ... A61B 5/0035; A61B 5/0044; A61B 5/0086; A61B 5/0095; A61B 5/02007;
(Continued)

(56) References Cited

U.S. PATENT DOCUMENTS 4,917,097 A   4/1990   Proudian et al.
6,013,032 A   1/2000   Savord
(Continued)

FOREIGN PATENT DOCUMENTS

CN   102743191 A   10/2012
CN   103385758 A   11/2013
(Continued)

OTHER PUBLICATIONS

Bao-Yu et al., Design and fabrication of an integrated intravascular ultrasound/photoacoustic scan head. Proceedings Spie. 2010;7564. 11 pages.
(Continued)

*Primary Examiner* — Sean A Frith
(74) *Attorney, Agent, or Firm* — Neal, Gerber & Eisenberg LLP (57) ABSTRACT

A catheter-based imaging apparatus comprises a catheter having a proximal end and a distal end. An optical emitter is configured to emit optical excitation signals from a distal portion of the catheter. One or more ultrasound transducers are configured for: (a) transmission of acoustic excitation signals from the distal portion of the catheter; and (b) detection of ultrasound response signals from an object of interest at or near to the distal portion of the catheter at frequencies which include a lower receive frequency at least as low as 10 MHz and a higher receive frequency at least as high as 35 MHz. The one or more ultrasound transducers are thereby configured to detect response signals comprising photoacoustic response signals from the object of interest at
(Continued)

the lower receive frequency and high resolution imaging signals from the object of interest at the higher receive frequency.

12 Claims, 6 Drawing Sheets

(51) Int. Cl.
*A61B 8/00* (2006.01)
*A61B 8/08* (2006.01)
*A61B 8/12* (2006.01)
*B06B 1/06* (2006.01)
*G01S 15/89* (2006.01)

(52) U.S. Cl.
CPC ........ *A61B 5/0095* (2013.01); *A61B 5/02007* (2013.01); *A61B 5/4869* (2013.01); *A61B 5/6852* (2013.01); *A61B 8/0891* (2013.01); *A61B 8/12* (2013.01); *A61B 8/4416* (2013.01); *A61B 8/4477* (2013.01); *A61B 8/4483* (2013.01); *B06B 1/0688* (2013.01); *A61B 5/7225* (2013.01); *A61B 8/483* (2013.01); *G01S 15/8956* (2013.01)

(58) Field of Classification Search
CPC ... A61B 5/4869; A61B 5/6852; A61B 8/0891; A61B 8/12; A61B 8/4416; A61B 8/4477; A61B 8/4483; A61B 5/7225; A61B 8/483; B06B 1/0688; G01S 15/8956
See application file for complete search history.

(56) References Cited

U.S. PATENT DOCUMENTS

| | | | |
|---|---|---|---|
| 11,793,405 B2 * | 10/2023 | Van Soest | A61B 5/4869 |
| 2008/0203556 A1 | 8/2008 | Huang | |
| 2010/0179434 A1 | 7/2010 | Thornton | |
| 2011/0021924 A1 | 1/2011 | Sethuraman et al. | |
| 2011/0088477 A1 | 4/2011 | Someda et al. | |
| 2011/0275890 A1 | 11/2011 | Wang et al. | |
| 2011/0301458 A1 | 12/2011 | Li et al. | |
| 2012/0197113 A1 | 8/2012 | Courtney et al. | |
| 2012/0271170 A1 | 10/2012 | Emelianov et al. | |
| 2013/0301380 A1 | 11/2013 | Oraevsky et al. | |
| 2013/0338498 A1 | 12/2013 | Emelianov et al. | |
| 2014/0018660 A1 * | 1/2014 | Wada | B06B 1/0607 600/407 |
| 2014/0112107 A1 | 4/2014 | Guo et al. | |
| 2014/0180078 A1 | 6/2014 | Nair | |
| 2014/0187925 A1 | 7/2014 | Corl | |
| 2014/0236017 A1 | 8/2014 | Degertekin et al. | |
| 2014/0251017 A1 | 9/2014 | Kandori | |
| 2014/0276069 A1 | 9/2014 | Amble et al. | |
| 2014/0378811 A1 | 12/2014 | Nanaumi | |
| 2015/0057534 A1 | 2/2015 | Tsujita | |
| 2016/0310083 A1 | 10/2016 | Wang et al. | |

FOREIGN PATENT DOCUMENTS

| | | |
|---|---|---|
| JP | H02502078 A | 7/1990 |
| JP | 2004057524 A | 2/2004 |
| JP | 2013106822 A | 6/2013 |
| WO | 2006061829 A1 | 6/2006 |
| WO | 2008057573 A2 | 5/2008 |
| WO | 2016128359 A1 | 8/2016 |

OTHER PUBLICATIONS

Bao-Yu et al., Integrated intravascular ultrasound and photoacoustic imaging scan head. Optics Letters, Optical Society of America. 2010;35(17). 3 pages.

Buja et al., Role of inflammation in coronary plaque disruption. Circulation. 1994;89(1):503-505.

Chao et al., A single-cable PVDF Transducer Readout IC for Intravascular Photoacoustic Imaging. 2015 IEEE International Ultrasonics Symposium (IUS). 2015:1-4.

Choudhury et al., Molecular, Cellular and Functional Imaging of Atherothrombosis. Nat. Rev. Dur. Discov. 2004;3(11):913-25.

Daeichin et al. A Broadband Polyvinylidene Difluoride-Based Hydrophone with Integrated Readout Circuit for Intravascular Photoacoustic Imaging. Ultrasound in Medicine and Biology. 2016;42(5): 1239-43.

Diebold et al., Photoacoustic "Signatures" of Particulate Matter: Optical Production of Acoustic Monopole Radiation. Science 250 (4977) 1990. 101-104.

Gertsch et al., Toward characterizing the size of microscopic optical absorbers using optoacoustic emission spectroscopy. Proceedings of Spie. 2010. 11 pages.

Hysi et al., Photoacoustic radio-frequency spectroscopy (PA-RFS): A technique for monitoring absorber size and concentration. Proc. of SPIE vol. 8581. 2013. 6 pages.

International Preliminary Report on Patentability for International Application No. PCT/EP2016/052639 dated Aug. 24, 2017.

International Search Report and Written Opinion for International Application No. PCT/EP2016/052639 dated Apr. 29, 2016.

Jansen et al., Intravascular photoacoustic imaging of human coronary atherosclerosis. Opt. Lett. 36(5):597-599. 2011.

Jansen et al., Intravascular Photoacoustic Imaging: A New Tool for Vulnerable Plaque Identification. Ultrasound in Medicine & Biology 40 (6), 1037-1048, 2014.

Jansen et al., Lipid detection in atherosclerotic human coronaries by spectroscopic intravascular photoacoustic imaging. Optics Express 21 (18), 21472-21484, 2013.

Jansen et al., Spectroscopic intravascular photoacoustic imaging of lipids in atherosclerosis. Journal of Biomedical Optics, S P I E International Society for Optical Engineering. 2014;19(2). 10 pages.

Japanese communication for Japanese Application No. 2017-540900 dated Oct. 8, 2019.

Karpiouk, A., et al., "Feasibility of in vivo intravascular photoacoustic imaging using integrated ultrasound and photoacoustic imaging catheter" Journal of Biomedical Optics. vol. 17(9), 2012. p. 1-6 (Year: 2012).

Kumon et al., Frequency-domain analysis of photoacoustic imaging data from prostate adenocarcinoma tumors in a murine model, Ultrasound Med. Biol. 37 (5), 834-839, 2011.

Libby et al., The vascular biology of atherosclerosis and imaging targets. Vascular Biology of Atherosclerosis. J. Nucl. Med. 1 (51), 15, 2010. 6 pages.

Libby, Inflammation in atherosclerosis. Nature Publishing Group. 2002;420:868-74.

Lloyd-Jones et al., Heart Disease and Stroke Statistics 2009 Update: A Report From the American Heart Association Statistics Committee and Stroke Statistics Subcommittee. Circulation 119 (3), e21-e181, 2009.

Ma et al., A Preliminary Engineering Design of Intravascular Dual-Frequency Transducers for Contrast-Enhanced Acoustic Angiography and Molecular Imaging, IEEE Trans. Ultrason. Ferroelectr. Freq. Control 61 (5), 870-880, 2014.

Ma, T., et al."'Multi-Frequency Intravascular Ultrasound (IVUS) Imaging'" IEEE Transactions on Ultrasonics, Ferroelectrics and Frequency Control. vol. 62(1), 2015. p. 97-107 (Year: 2015).

Naghavi et al., From Vulnerable Plaque to Vulnerable Patient: A Call for New Definitions and Risk Assessment Strategies: Part II. Circulation 108 (14), 1664-1672, 2003.

Puri et al., Exploring coronary atherosclerosis with intravascular imaging. Int. J. Cardiol. 2013;168(2):670-79.

Sheu, Y., et al ,"Image Reconstruction in Intravascular Photoacoustic Imaging" IEEE Transactions on Ultrasonics, Ferroelectrics, and Frequency Control. vol. 58(10), 2011. p. 2067-2077 (Year: 2011).

Shriram et al., Intravascular Photoacoustic Imaging Using an IVUS Imaging Catheter. IEEE Transactions on Ultrasonics. Ferroelectrics and frequency control. 2007;53(5):978-86.

(56) References Cited

OTHER PUBLICATIONS

Treeby et al., k-Wave: MATLAB toolbox for the simulation and reconstruction of photo acoustic wave fields. Journal of Biomedical Optics. 2010;15(2): 1-12.
Wang et al., Intravascular photoacoustic imaging of lipid in atherosclerotic plaques in the presence of luminal blood. Opt. Lett. 37 (7), 1244-1246, 2012.
Wang et al., Label-Free Bond-Selective Imaging by Listening to Vibrationally Excited Molecules. Phys. Rev. Lett. 106 (23), 10, 2011. 8 pages.
Wang et al., Spectroscopic Imaging of Deep Tissue through Photoacoustic Detection of Molecular Vibration. J. Phys. Chem. Lett. 4 (13), 2177-2185, 2013.

\* cited by examiner

INTRAVASCULAR PHOTOACOUSTIC IMAGING

CROSS-REFERENCE TO RELATED APPLICATION

This application is a continuation of U.S. patent application Ser. No. 15/549,552, filed Aug. 8, 2017, which national stage entry pursuant to 35 U.S.C. § 371 of International Application No. PCT/EP2016/052639, filed on Feb. 8, 2016, which claims priority to GB Patent Application No. 1502101.7, filed Feb. 9, 2015, the contents of all of which are fully incorporated herein by reference.

The present invention relates to methods and apparatus for intravascular photoacoustic imaging and in particular though not exclusively to such methods as applied to spectroscopic photoacoustic imaging, ultrasound imaging and ultrasound harmonic or contrast imaging.

A major cause of death is cardiovascular disease [1]. A substantial proportion of cardiac deaths are due to acute coronary syndromes. The majority of these fatal acute coronary syndromes are caused by ruptures of vulnerable atherosclerotic plaques and thrombosis [2-5].

The identification of vulnerable atherosclerotic plaques in the coronary artery is emerging as an important tool for guiding percutaneous coronary interventions. The structure and composition of the plaque are significant determinants of its vulnerability.

Current ultrasound imaging modalities have limitations in their ability to assist in useful analysis. For example, it is reported that intravascular ultrasound imaging is unable to distinguish different chemical components [6]; intravascular near infrared spectroscopy cannot provide depth-resolved spatial resolution; intravascular fluorescence imaging provides only shallow imaging depth; and intravascular optical coherence tomography provides neither sufficient imaging depth nor chemical selectivity. It would be desirable to provide an imaging tool which can be reliably and accurately used detect a vulnerable plaque in live patients [7].

It is an object of the present invention to provide an improved photoacoustic imaging tool.

According to one aspect, the present invention provides a catheter-based imaging apparatus comprising:
 a catheter having a proximal end and a distal end;
 an optical emitter configured to emit optical excitation signals from a distal portion of the catheter;
 one or more ultrasound transducers configured for:
 (a) transmission of acoustic excitation signals from the distal portion of the catheter;
 (b) detection of ultrasound response signals from an object of interest at or near to the distal portion of the catheter at frequencies which include a lower receive frequency at least as low as 10 MHz and a higher receive frequency at least as high as 35 MHz, the one or more ultrasound transducers thereby being configured to detect response signals comprising photoacoustic response signals from the object of interest at the lower receive frequency and high resolution imaging signals from the object of interest at the higher receive frequency.

The one or more ultrasound transducers may be configured to be operable at a frequency range which encompasses a lower receive frequency at least as low as 4 MHz and/or a higher receive frequency at least as high as 40 MHz. The one or more ultrasound transducers may comprise a first transducer operable in the range 2 to 20 MHz and a second transducer operable in the range 20 to 60 MHz. A first ultrasound transducer may have a peak detection sensitivity in the range 2 to 10 MHz or 2 to 4 MHz and a second transducer may have a peak detection sensitivity in the range 35 to 60 MHz. The one or more ultrasound transducers may comprise a first transducer operable in a lower frequency range and a second transducer operable in a higher frequency range. The first transducer may comprise a piezoelectric polymer transducer or a piezoelectric composite transducer and the second transducer may comprise a piezoelectric ceramic transducer or a piezoelectric composite transducer. The polymer transducer may be a PVDF transducer or a PVTrF transducer. The one or more ultrasound transducers may comprise a first transducer operable in a lower frequency range and a second transducer operable in a higher frequency range and the first and second transducers may be mounted on a common substrate in the distal portion of the catheter.

The catheter-based imaging apparatus may include a charge readout circuit mounted on the common substrate. The second transducer may form a substrate on which the first transducer is mounted or vice versa. At least one of the transducers may comprise a PVDF transducer and further include a charge readout circuit, the PVDF transducer and the charge readout circuit being disposed on a common substrate. The charge readout circuit may comprise a current-to-voltage converter on the common substrate in the distal portion of the catheter. The charge readout circuit may have an output coupled to a coaxial cable extending between the distal end and the proximal end of the catheter. The output of the charge readout circuit may include a source follower configured to be biased by a current source coupled to the coaxial cable at the proximal end of the catheter. The charge readout circuit may further include a DC current mirror supplied by the current source and providing a bias supply to a transimpedance amplifier in the current to voltage converter. The charge readout circuit and the PVDF transducer may both be powered by a current source at the distal end of the catheter by way of the coaxial cable.

The catheter-based imaging apparatus may include a control module configured to drive the optical emitter to emit said optical excitation signals;
 a control module configured to drive said one or more ultrasound transducers to transmit said acoustic excitation signals; and
 an analysis module coupled to an output of the one or more transducers and configured to receive said response signals from said one or more transducers and to determine first image data based on said photoacoustic response signals in a first frequency band and second image data based on the acoustic response signals in a second frequency band different from the first frequency band.

The analysis module may be configured to identify lipids in said object of interest.

According to another aspect, the present invention provides a method of obtaining intravascular photoacoustic image data comprising:
 emitting, from a distal portion of a catheter-mounted optical emitter, an optical excitation signal directed to a target region of an object of interest;
 emitting, from the distal portion of the catheter, by one or more catheter-mounted ultrasound transducers, an acoustic excitation signal directed to the target region of the object of interest;
 detecting, by the one or more catheter-mounted ultrasound transducers, a photoacoustic ultrasound response signal at a lower receive frequency less than or equal to 10 MHz and an ultrasound imaging response signal at a higher receive frequency greater than or equal to 35 MHz;

using the response signals to determine a chemical composition of the target area of the object of interest and an image of the target area of the object of interest.

Embodiments of the present invention will now be described by way of example and with reference to the accompanying drawings in which.

Photoacoustic imaging, and particularly spectral photoacoustic imaging, may be a new modality capable of detecting and locating lipid components in a vessel wall with reasonably large imaging depth [8-11]. Spectroscopic photoacoustic (sPA) imaging can visualize atherosclerotic plaque composition on the basis of optical absorption contrast. Photoacoustic imaging is based on excitation of objects of interest, such as tissue, with short light (e.g. laser) pulses and consequent detection of acoustic signal modulation generated as a result of thermal expansion of the target objects of interest. Light absorbers that are irradiated by pulsed light and emit acoustic waves are herein referred to as photoacoustic sources. This imaging technique therefore benefits from optical absorption properties of tissue composition as contrast. The frequency range of the photoacoustic signal is correlated with the structural tissue properties.

As photoacoustic signals can be weak, it is important to match the transducer sensitivity to the signal frequency content for in-vivo imaging. For optimal detection of photoacoustic signals, a transducer with a centre frequency below 15 MHz is desirable. However, to produce high resolution intravascular ultrasound images for accurate location of the photoacoustic signals, it is optimal to use a transducer with a centre frequency substantially above this.

Recently, a preliminary engineering design for dual-frequency transducers for IVUS catheters has been suggested by Ma et al [12]. In this paper, a dual-frequency transducer arrangement with aperture size of 0.6×3 mm for an IVUS probe was presented. The transducer elements consisted of lead magnesium niobate-lead titanate. The low frequency transmitting element had a centre frequency of 6.5 MHz and a size of 0.6×3 mm. The high frequency element was mounted on the top of the low frequency transducer with a centre frequency of 30 MHz and size of 0.6×0.5 mm with −6 dB fractional bandwidth of 58.6%. This dual-frequency IVUS catheter was particularly designed for contrast-enhanced IVUS imaging in which the low frequency elements were used for exciting ultrasound contrast agents close to their resonance frequency and the high frequency element was used to receive the super-harmonic responses of the agents.

The inventors have particularly recognised that a dual frequency approach may be developed for use in an intravascular photoacoustic imaging environment to great benefit.

However, despite increasing the bandwidth of IVUS imaging with a dual-frequency technique and promising in vitro results presented in Ma et al, the large rigid size of the catheter and large noise level are challenges to be overcome for translating the technology into clinics. Also, in intravascular photoacoustic imaging applications, the sensitivity of the ultrasound transducer element in the receive mode is crucial.

As described with reference to FIG. 1, in an ex vivo setup, the frequency components of photoacoustic signals from human coronary arteries were acquired in spectroscopy experiments and investigated. Utilizing a broadband PVDF transducer (−3 dB one-way bandwidth of 10-35 MHz) with a 1 mm needle hydrophone (calibrated for 2-20 MHz) in the setup, we covered a large frequency range (2-35 MHz) for receiving the photoacoustic signal. Spectroscopic photoacoustic (sPA) imaging was performed at wavelengths ranging from 1125 to 1275 nm with steps of 2 nm, allowing discrimination between plaque lipids and adventitial tissue. Guided by the sPA imaging, the frequency content of the photoacoustic signal from the plaque lipids was quantified. We also performed a series of simulations using a k-Wave toolbox to define the relation between photoacoustic source size and main frequency component and the amplitude of the photoacoustic signal in that frequency. Moreover, using the initial pressure source obtained from human coronary plaque histological slices which were stained for fat (Oil Red O), we modelled the photoacoustic responses of the intraplaque lipids. Based on the results found in the experiment and simulation studies, a novel intravascular photoacoustic (IVPA) catheter configuration has been designed which covers a frequency range of 2 to 60 MHz. This range is ideally adapted for receiving the photoacoustic signals particularly at frequencies below 15 MHz while maintaining the high resolution IVUS images from the higher end of the frequency range.

Figure 1:
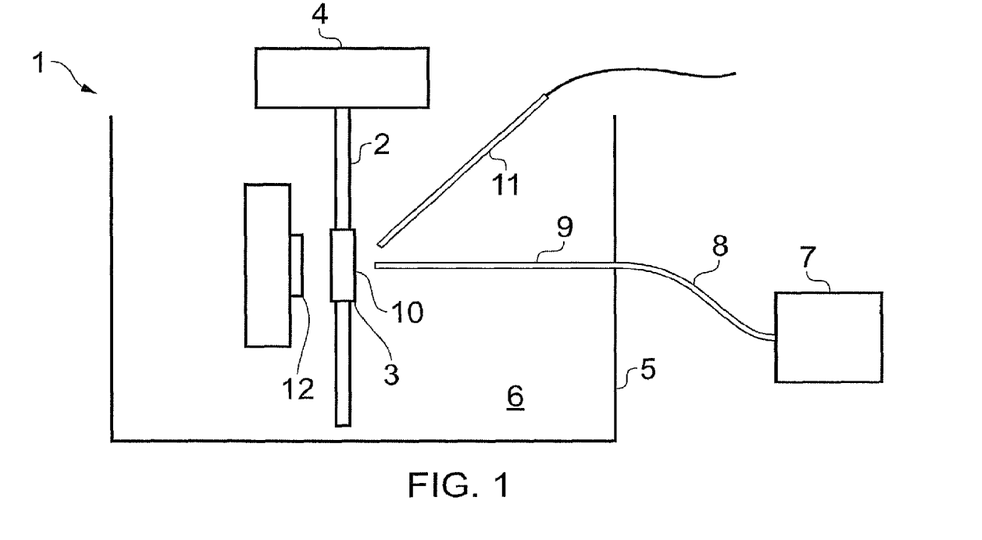
FIG. 1 shows a schematic diagram of experimental apparatus for an ex vivo analysis of the photoacoustic response of plaque regions in atherosclerotic coronary arteries.

With reference to FIG. 1, in the ex-vivo experiment using the apparatus 1, four human coronary arteries were cut open and placed on a holder 2 with a window 3 of size of 5×5 mm. The holder 2 was mounted on a positioning system 4 (MP 63-25-DC, Steinmeyer GmbH & Co. KG, Albstadt, Germany) in order to scan different locations on the sample (object of interest) 10. The whole sample was put in a water tank 5 filled with saline solution 6 at room temperature. A tuneable laser 7 (Vibrant B/355-II, OPOTEK, Santa Clara, CA, USA) served as an optical emitter which provided optical excitation radiation (pulse width 5 ns, repetition rate 10 Hz, pulse energy 2 mJ) for photoacoustic imaging. A tapered multimode optical fibre 8 (Oxford Electronics, Four Marks, UK; input diameter 1 mm; output diameter 360 µm) coupled the laser light to a custom built 400 urn diameter optical probe 9 for light delivery to the sample 10. In some experiments, the optical probe 9 was mounted adjacent to a needle hydrophone 11 and on the opposite side of the sample 10 to a PVDF high frequency transducer 12. In other experiments, the needle hydrophone 11 was placed on the opposite side of the sample to the optical probe 9. We first used the needle hydrophone 11 and then the PVDF transducer 12 to receive photoacoustic spectral data from the same tissue locations. The sample 10 was placed at the focus (13 mm) of the transducer 12, and 13 mm away from the hydrophone 11. The optical probe 9 was kept 5 mm away from the sample 10. To scan the sample tissue, the sample holder 2 was moved with the motorized translation stage 4.

The received photoacoustic signals were amplified by a 43 dB amplifier (AU1263, Miteq, Hauppauge, NY, USA) and digitized at sample frequency of 350 MHz by 12-bit data acquisition card (Acqiris DP310, Agilent, Santa Clara, CA, USA).

The sPA imaging was performed at optical excitation wavelengths ranging from 1125 to 1275 nm with steps of 2 nm, allowing localization of the plaque region and discrimination between plaque lipids and peri-adventitial fat tissue [13]. To improve photoacoustic signal to noise ratio, 32 photoacoustic signals were collected and averaged at each wavelength. In each artery piece, photoacoustic spectra from plaque were collected at not less than 5 different locations inside the plaque region. After imaging, Oil Red O (ORO) staining was performed at the imaging plane to identify intraplaque lipids and peri-adventitial lipids (lipids are stained red in ORO staining).

Simulations

The MATLAB k-Wave toolbox was used to simulate the time-domain photoacoustic signal, and a fast Fourier transform (FFT) was applied to obtain the frequency domain spectrum. k-Wave is a freely available 3rd-party toolbox for MATLAB which uses a k-space pseudo-spectral solution method for the time domain simulation of photoacoustic wave propagation to couple first-order acoustic equations for homogenous and heterogeneous media [14]. Assuming an isotropic linear sound propagation in the medium, the acoustic pressure, p, acoustic particle velocity, u, and acoustic density, ρ, can be quantified according to Newton's second law (also called momentum conservation law, the equation of motion or Euler's equation), mass conservation law (also called the continuity equation), and an equation of state:

$$\partial u/\partial t = -(1/\rho_0)\nabla p \quad (1)$$

$$\partial p/\partial t = -\rho_0 \nabla \cdot u \quad (2)$$

$$p = c^2 \rho \quad (3)$$

where c is the thermodynamic sound speed. Equations 1, 2 and 3 can be combined to give the well-known acoustic wave equation for heterogeneous media:

$$[\rho_0 \nabla \cdot (1/\rho_0) - (1/c^2)(\partial^2/\partial t^2)]p = 0 \quad (4)$$

where the pressure, p, depends on both the position, x, and time, t, as they can vary.

Discrete versions of these equations are solved using the Fast Fourier Transform (FFT) and a k-space (wavenumber domain) pseudo-spectral solution method to compute the pressure field at each time step in the k-wave toolbox [14].

In our k-Wave simulations, first a Gaussian pulse beam was uniformly applied to target discs with radiuses from 1 to 120 µm (as simple photoacoustic sources), and a single-element sensor was used to detect the acoustic wave within a two-dimensional homogeneous medium. To simulate the effects of the photoacoustic source size on the main frequency component of its photoacoustic signals, the FFTs of the photoacoustic signals were calculated to detect maximum amplitude of the photoacoustic signals and the frequency in which the responses had their maximum amplitude.

Next the initial pressure source was obtained from human coronary plaque histological images which were stained for fat. First fat staining in the histological images were segmented using a custom-made filtering method based on the RGB colours of the image. The sizes of the fatty structures were detected and the data were resampled according to the grid size and the size of the input image. To account for the limited bandpass of the transducer in the experiments, the impulse response of the transducer were measured with a calibrated needle hydrophone and then applied to the simulated photoacoustic signals in the frequency domain.

Data Analysis

All the stored spectral data were firstly digitally bandpass filtered. The data from needle hydrophone 11 were filtered from 1 to 15 MHz (−4 dB bandwidth) and the data from PVDF transducer were filtered from 10 to 35 MHz (−3 dB one-way bandwidth), using a 100th order zero-phase forward and reverse finite impulse response (FIR) filter. By comparing the acquired photoacoustic spectra with the reference photoacoustic spectra of plaque lipids and peri-adventitial fat, we could identify the photoacoustic signal which belongs to the intraplaque lipid. Then we isolated this part of the photoacoustic signal at the wavelength where lipids effectively absorb light (e.g. 1205 nm). The isolated photoacoustic signal part was first filtered to remove the DC component. Then a Tukey window was applied on the filtered signals before they were Fourier transformed.

In order to analyze the recorded photoacoustic signals over the full frequency range (2-35 MHz), the data recorded by the calibrated hydrophone (2-15 MHz) and the calibrated PVDF transducer (10-35 MHz) were stitched together. Since there was a frequency range overlap (10-15 MHz) within the sensitive range of both the hydrophone and the PVDF transducer, the stitching was performed at frequency of 13 MHz which is within the −3 dB one-way bandwidth of both detectors. Then we calculated a frequency in which the amplitude of the photoacoustic signal was maximum as well as the percentage of the power spectra for the frequency range of 2-35 MHz.

Figure 2:
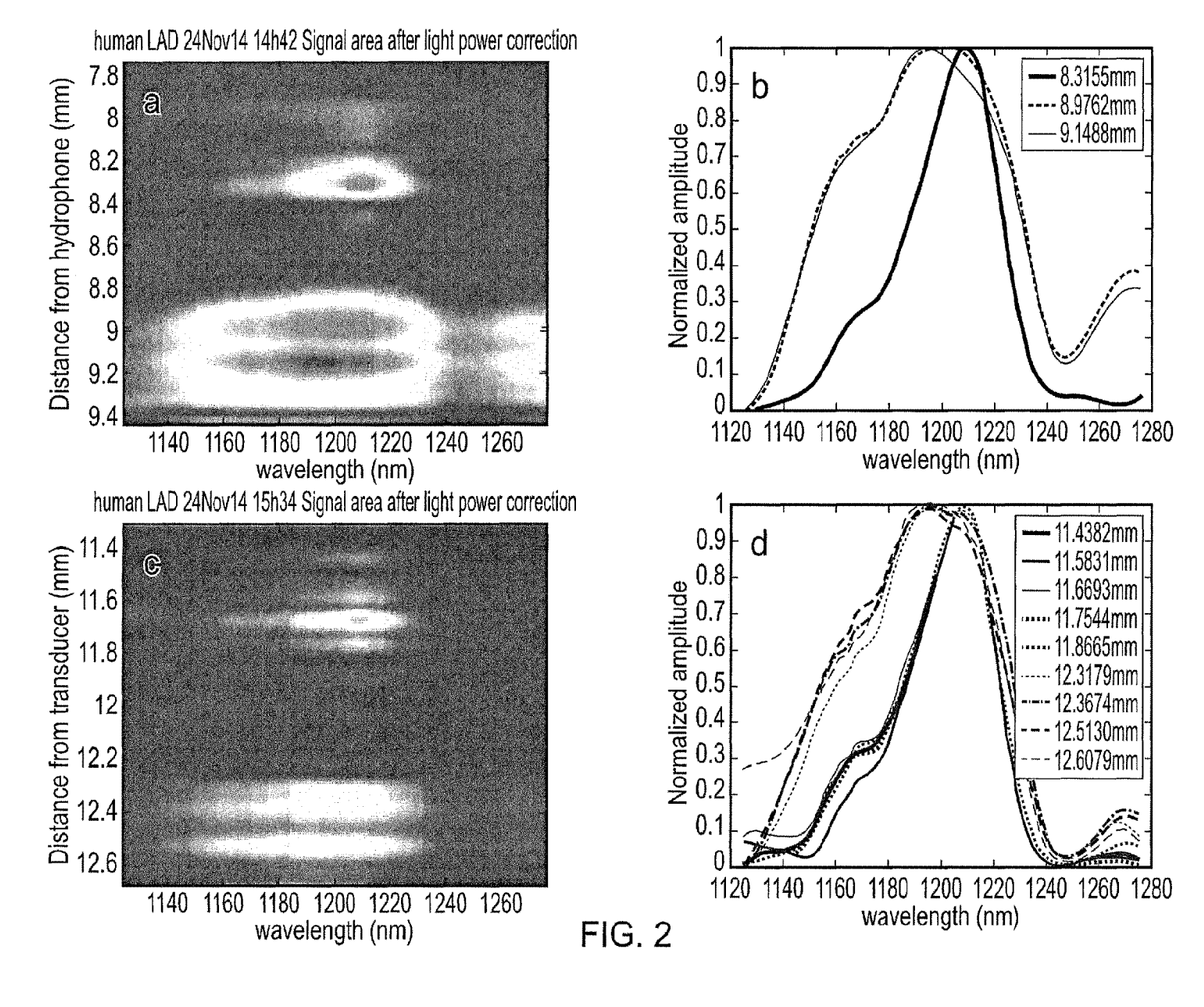
FIG. 2 shows spectroscopic photoacoustic imaging results from the experimental apparatus of FIG. 1 showing acoustic signal intensity after light power correction as a function of distance from the catheter and optical excitation wavelength (FIGS. 2*a* and 2*c*) and normalised acoustic signal amplitude as a function of optical excitation wavelength (FIGS. 2*b* and 2*d*)

Results of sPA imaging of an atherosclerotic coronary artery sample are depicted in FIG. 2. By comparing the received photoacoustic spectra data to the reference spectra [15], we can easily identify the signal generated from the atherosclerotic plaque.

FIGS. 2a and 2b show the results of spectroscopic photoacoustic imaging of an atherosclerotic coronary artery sample ex vivo acquired with the hydrophone 11. FIG. 2a shows photoacoustic response signal amplitude by colour as a function of optical excitation emission wavelength (x axis) and distance from the hydrophone (y axis). The photoacoustic signals are integrated over the sensitive frequency bandwidth of the hydrophone (2 to 20 MHz). FIG. 2b shows the amplitude of the acoustic response signal as a function of optical excitation emission wavelength.

FIGS. 2c and 2d show corresponding results acquired with the PVDF transducer receiving the photoacoustic response to the optical excitation signals, in which the y-axis represents distance from the surface of the PVDF transducer 12. The photoacoustic response is integrated over the sensitive frequency bandwidth of the transducer, e.g. 10 to 35 MHz. The photoacoustic response from atherosclerotic plaque, peri-adventitial fat, and other tissues has a characteristic dependence on optical excitation wavelength. We observed that this response also changes with the acoustic frequency band. The photoacoustic spectra may be compared to reference photoacoustic spectra to identify specific chemical components.

Figure 3:
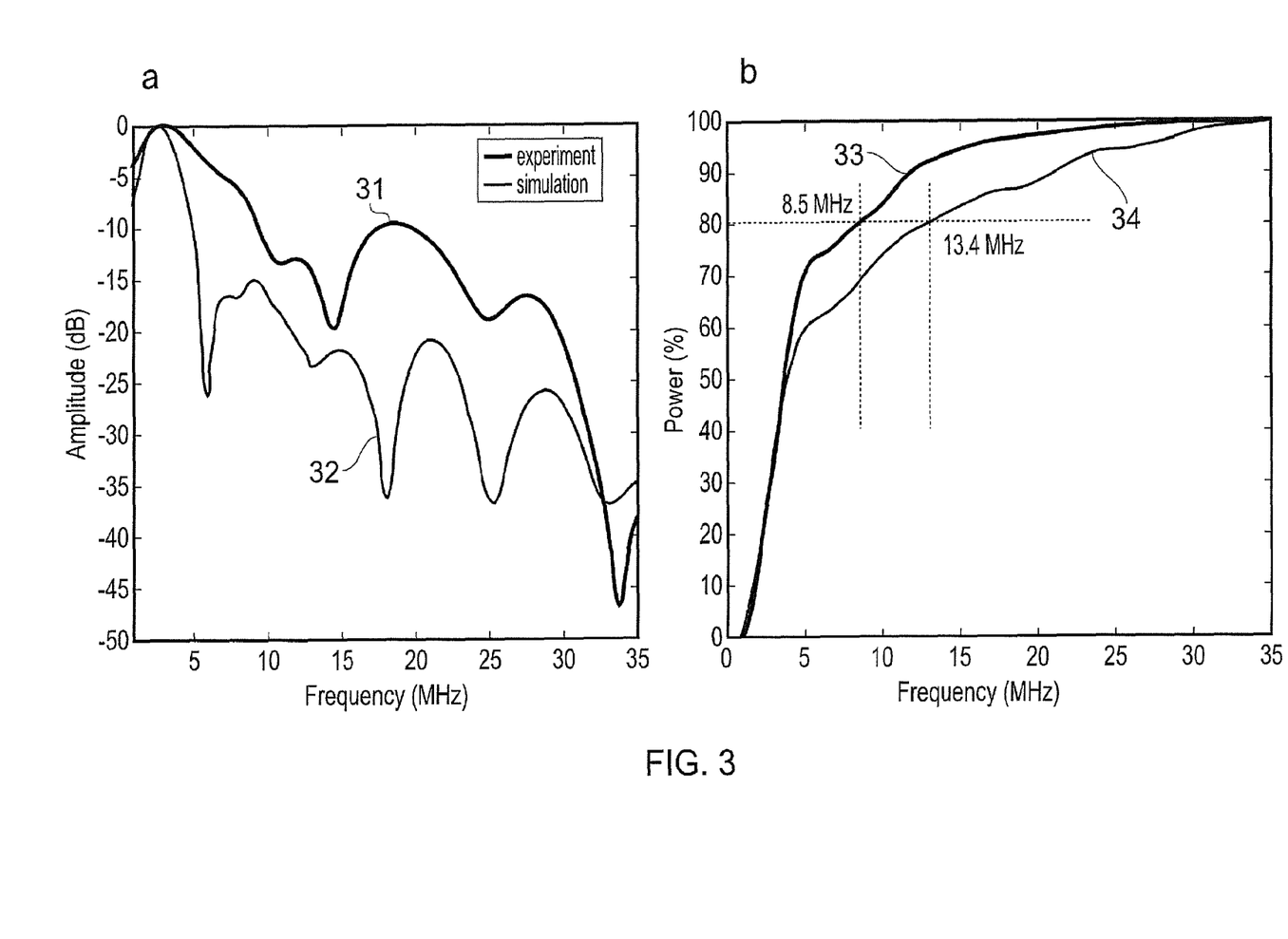
FIG. 3 shows acoustic frequency analysis of the signal obtained from the experimental apparatus of FIG. 1 compared with simulation results, showing maximum amplitude of the photoacoustic response signal amplitude as a function of acoustic frequency and power of the photoacoustic response signal as a function of acoustic frequency.

The acoustic spectroscopy of such a sample as an example is presented and compared to the simulation results in FIG. 3. FIG. 3 shows an acoustic spectroscopy image of an atherosclerotic coronary artery sample compared to the simulation results. Trace 31 shows the experimental amplitude of acoustic response as a function of ultrasound frequency, to optical excitation at a wavelength optimised for absorption by atherosclerotic plaque lipid (e.g. approximately 1195 mm), compared with the simulation results in trace 32. Trace 33 shows the experimental acoustic power as a function of ultrasound frequency, to optical excitation at the wavelength optimised for absorption by atherosclerotic plaque. FIG. 3 shows that the maximum amplitude of the photoacoustic signal in both the experiment and simulation studies are at frequencies below 5 MHz. An analysis of 36 photoacoustic signals from human atherosclerotic plaque demonstrated that 60% of the photoacoustic signal power is at frequencies<5 MHz (median), and 80% of the photoacoustic signal power lies below 10 MHz (median).

Simulations

Figure 4:
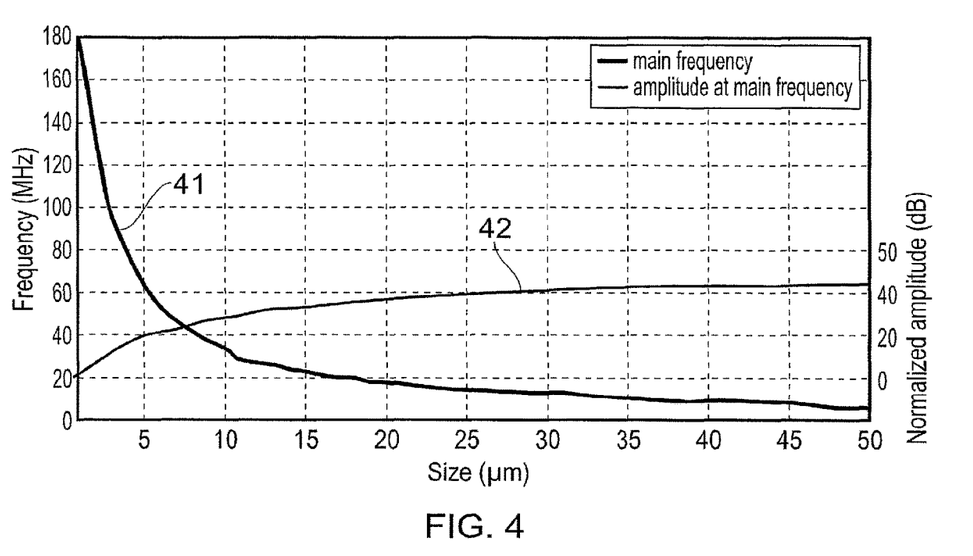
FIG. 4 shows the photoacoustic response main frequency component and the corresponding amplitude as a function of the disc diameter of simulated photoacoustic sources.

Firstly, photoacoustic signals from single spherical photoacoustic sources with radii from 1 to 50 μm were simulated. The fast Fourier transform of the photoacoustic signal was calculated to detect maximum amplitude of the photoacoustic signal and the frequency at which the responses had their maximum amplitude. The results are plotted in FIG. 4. Trace 41 shows the main frequency component and trace 42 shows the corresponding amplitude of the photoacoustic signal as a function of photoacoustic source disc diameter, varying from 1 to 50 μm. As expected, the major frequency component of the photoacoustic signals from the disks decreases quadratically in respect to the disk size. It can be seen that the major frequency component is below 15 MHz for disks with radii larger than 50 μm.

Figure 5:
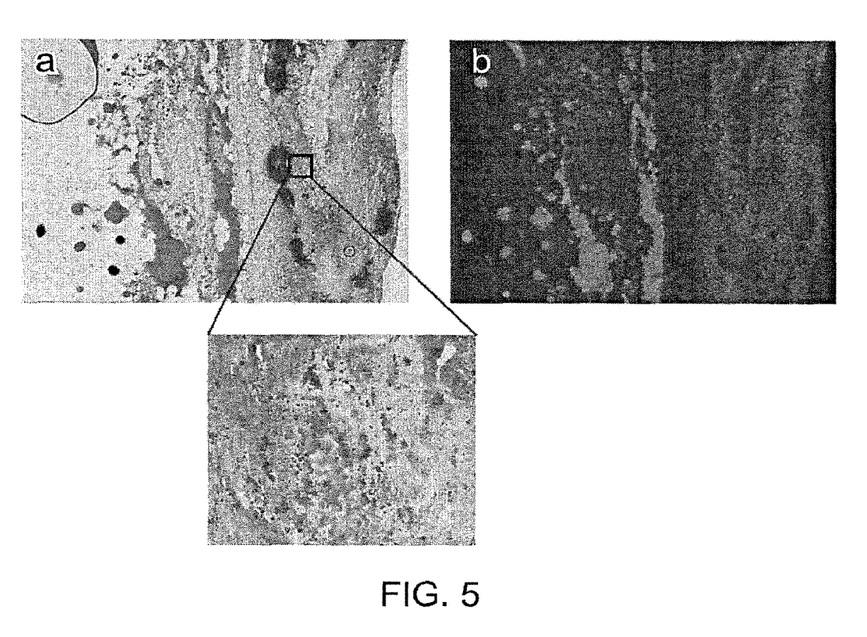
FIG. 5 shows images of a histology slice which is stained for lipids (FIG. 5*a*) and the image after applying the lipid segmentation (FIG. 5*b*)

Next the initial pressure source was obtained from human coronary plaque histological images which were stained for fat. FIG. 5 shows an example of a histology slice which is stained (ORO) for lipids (FIG. 5a) and the image after applying the lipid segmentation (FIG. 5b) based on RGB colors using a custom-made segmentation tool. The inset to FIG. 5a shows the intraplaque lipids. The photoacoustic signal of such a sample is presented and compared to its experimental data in FIG. 3.

The simulation results confirm the experimental finding that more than 80% of the photoacoustic energy of the coronary plaque lipids lies in the frequency band below 15 MHz. This frequency information guides the choice of a transducer element used for IVPA catheter fabrication and may be used for characterizing the size and distribution of intraplaque lipids. The results indicate that the spectral parameters of photoacoustic signals are sensitive to changes in size and concentration of the photoacoustic sources. More samples of human atherosclerosis plaques may be used to establish the range of lipid structure sizes. The ex vivo and simulation results show that the main energy of the photoacoustic signals from the plaque lipid is significantly below currently used frequencies in IVPA. However, poor resolution of ultrasound transducer elements with such low centre frequency limits the use of these ultrasound transducers for IVPA and IVUS imaging. High-frequency transducers have limited sensitivity to intravascular photoacoustic signals. Thus, it is proposed to provide a catheter-based photoacoustic imaging system configured to provide one or more transducers operable within a frequency range which encompasses at least as low as 10 MHz and at least as high as 35 MHz.

Theoretical solutions of the wave equation for simple geometries predict that the photoacoustic pressure in the frequency domain is proportional to the radius of the absorber squared [16]. This suggests that larger spherical particles will emit photoacoustic pressure waves with higher amplitude compared to smaller particles. The relationship between the source size and the amplitude and frequency of the photoacoustic signal has been suggested to distinguish particle sizes in micron range before [17-19]. Moreover, it is worth noting that the large amplitude photoacoustic signal of the bigger structures at lower frequencies can mask the weaker signal of the smaller structures at higher frequencies if the space between them is not enough. For instance, the maximum amplitude of the photoacoustic signal for a disk with a radius of 50 μm which is around 15 MHz is more than 20 dB higher than that for a disk with radius of 5 μm with maximum amplitude at around 60 MHz.

Despite the fact that the mechanism of ultrasound wave generation differs when comparing backscattered ultrasound and photoacoustic emitted ultrasound, the detection of the backscattered and emitted photoacoustic signals is identical which suggests that spectroscopic analysis can reveal important information about the sizes and concentrations of photoacoustic sources. It should be noted that the transducer bandwidth would significantly affect detection of many of the frequencies generated by thermoelastic expansion of an optical absorber. By taking into account a transducer with a finite bandwidth, many of the frequencies present in the spectra will be filtered out due to the inherent filtering nature of ultrasound transducers. Furthermore, by normalizing the spectra, transducer-dependent settings during the measurement can be removed. This provides a set of parameters that can be quantitatively related to tissue properties. Frequency analysis of the photoacoustic signal has already been shown to play an important role in tissue characterization for monitoring the size of absorbers during the presence of various types of carcinomas as well as during chemotherapeutic treatments of tumours but no such investigation has been done on atherosclerosis plaques yet.

Based on our frequency analysis of intraplaque lipid photoacoustic signals, it is expected that the sensitivity of IVPA imaging for intraplaque lipids will be significantly improved if ultrasound transducers with larger bandwidth which covers the lower frequencies (2-15 MHz) are used.

In this disclosure, we propose a novel IVPA catheter configuration for increasing bandwidth and covering the low frequency range of ultrasound response, while maintaining high resolution for IVUS images at the same time. A preferred arrangement combines a broadband low frequency PVDF transducer operable in a range from 2 to 20 MHz with a conventional IVUS transducer element operable in the range 20 to 60 MHz, to cover a broad range of frequencies (2 to 60 MHz) in reception. Smaller frequency ranges may still achieve significant benefit, as discussed later. In a preferred arrangement, the low frequency PVDF element need only be used in receive mode. The conventional IVUS transducer may be used to create high resolution images.

Figure 8:
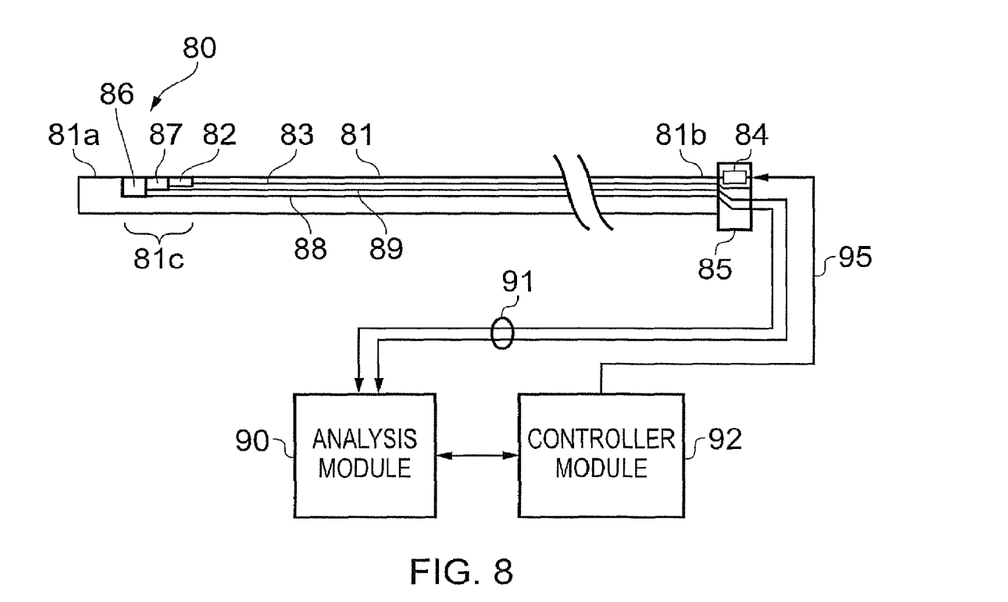
FIG. 8 shows a schematic diagram of a catheter-based photoacoustic imaging apparatus.

With reference to FIG. 8, there is shown a catheter-based imaging apparatus 80 comprising a catheter 81 having a distal end 81a and a proximal end 81b. The catheter 81 is configured to be of a size and flexibility compatible with introduction into a human or animal vascular system to reach an object of interest within the vascular system.

At a distal portion 81c of the catheter 81, located between the distal end 81a and the proximal end 81b, is provided an optical emitter 82 which is configured to emit optical radiation from the distal portion of the catheter. The optical emitter 82 may comprise the end of a light pipe such as an optical fibre 83 which extends along the catheter 81 to a light emitting device 84 disposed at or beyond the proximal end 81b of the catheter. For example, the light emitting device 84 could be located within a connector 85 disposed at the proximal end 81b, or in a control module 92 coupled thereto by cable/fibre 95. The optical emitter 82 may alternatively comprise a light source such as a light emitting diode/laser diode disposed in the distal portion 81c of the catheter itself. The optical emitter 82 may be a single optical emitter or an array of optical emitters.

Also disposed in the distal portion 81c of the catheter 81 is a first transducer element 86 or transducer array (both alternatives being referred to herein as "transducer") which is particularly adapted to be operable within a frequency range which encompasses at least a receive frequency within the range 2 to 20 MHz. More preferably, the first transducer is operable with a receive frequency within the range 2 to 10 MHz, or even 2 to 4 MHz. The first transducer 86 is preferably configured such that it has a maximum or peak sensitivity for optimal detection of photoacoustic response signals emitted by target objects of interest when excited by optical excitation signals at selected wavelengths. Preferably, the peak detection sensitivity lies in the range 2 to 10 MHz, or more preferably 2 to 4 MHz. A further preferred configuration is for a first transducer element 86 which has a broadband receive frequency sensitivity extending over 2 to 15 MHz or 2 to 10 MHz. For example, when detecting a plaque lipid photoacoustic signal, an increase in signal to noise ratio of up to 20 dB may be achieved when the photoacoustic signal is recorded in the frequency range of 2 to 10 MHz compared to 20 to 35 MHz.

Also disposed in the distal portion 81c of the catheter 81 is a second transducer element 87 or transducer array (both alternatives being referred to herein as "transducer") which is particularly adapted to be operable within a frequency range which encompasses at least a receive frequency within the range 20 to 60 MHz. The second transducer element 87 is preferably configured such that it has a maximum or peak sensitivity for a high resolution acoustic imaging response from the object of interest. Preferably, the peak detection sensitivity lies in the range 35 to 60 MHz. In an example, assuming a single cycle transmit pulse of a frequency range 20 to 60 MHz, the a maximum axial resolution of 25 microns may be achievable, assuming the speed of sound in the medium to be 1500 m/s and wavelength in the range 25 to 75 microns.

The outputs of the first and second transducers 86, 87 are respectively coupled to an analysis module 90 via electrical leads 88, 89 extending through the catheter 81, and via the connector 85 to external leads 91. If the first and second transducers are impedance matched, e.g. both with high impedance, then they may both be connected to the same low noise amplifier and may share an output lead.

The first transducer 86 may be a polyvinylidene difluoride (PVDF) transducer or a polyvinylidene trifluoride (PVTrF) or composite transducer which may offer superior performance within the low frequency range of, for example 2 to 10 MHz, for detecting photoacoustic emissions from the target objects of interest. The second transducer 87 may be a piezoelectric ceramic transducer, such as a PZT (lead zirconium titanate) or PMN-PT (lead magnesium niobate-lead titanate) or composite transducer.

Capacitive micromachined ultrasonic transducer (CMUT) devices may alternatively be used.

A potential problem to overcome when using small polymer transducers such as PVDF or PVTrF transducers as may be required for use in the intravascular catheter 81 is an impedance mismatch between the polymer transducer 86 and the connecting cables 88. This can arise from a very low dielectric constant of, e.g. PVDF or PVTrF when provided in such a small size. A solution to this problem can be to use an application specific integrated circuit (ASIC) in very close proximity to the transducer 86, and which may provide a low-power single wire readout system for IVPA as described below.

Figure 6:
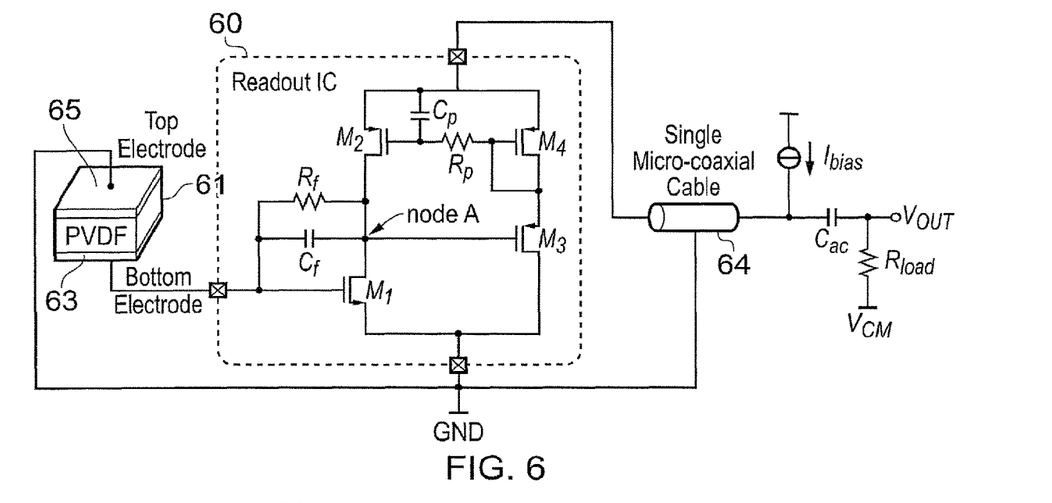
FIG. 6 is a schematic diagram of a readout circuit suitable for use within a catheter-based photoacoustic imaging apparatus.

FIG. 6 shows a block diagram of a single-wire IVUS readout circuit 60 useful in the catheter-based photoacoustic imaging apparatus of FIG. 8. Circuit 60 provides an interface between a catheter-mounted PVDF or PVTrF transducer 61 and the analysis module 90 which may be external to the catheter as shown in FIG. 8. The PVDF or PVTrF transducer 61 may be directly mounted on top of the readout circuit 60 which may be fabricated as a single integrated circuit. The transducer 61 and the readout circuit 60 are disposed in the distal portion 81c of the catheter 81 and electrically coupled to the analysis module 90 by a coaxial cable 64 extending along the catheter to its proximal end 81b and to the connector 85. In this respect, the coaxial cable 64 is an example of the connecting cable 88 of FIG. 8. The readout circuit 60 may be configured to locally process an acoustic response signal from the bottom electrode 63 of the transducer 61 and send the signal to the analysis module 90. In this configuration, only one cable 64 is required for the interconnection between the readout circuit 60 and the analysis module 90 which helps in reducing catheter diameter and eases system interconnections.

In the readout circuit 60, MOS transistor $M_1$, capacitor $C_f$ and resistor $R_f$ form a transimpedance amplifier (TIA) which converts the PVDF or PVTrF transducer output current to voltage. The gain of this amplifier is determined by the combined impedance of the feedback components, i.e. $C_f$ and $R_f$. By increasing the transimpedance, the noise contributions from succeeding circuits and cables are attenuated compared to the transducer 61 output. As such, the TIA also performs as a low-noise amplifier (LNA).

The output voltage of the TIA (node A in FIG. 6) is buffered by a source follower formed by transistor $M_3$ which provides a low output impedance to interface with the 50Ω coaxial cable 64. The source follower $M_3$ is biased by an external DC current source ($I_{bias}$) at the other end of coaxial cable 64 (e.g. at the catheter connector 85 or in an external control module 92. As the output impedance of the source follower $M_3$ is a function of its bias current, the output impedance of the readout circuit 60 can be fine-tuned by adjusting $I_{bias}$ to match the impedance of cable 64, thus reducing the signal reflection in the cable. (A micro-coaxial cable with a length of 3 to 4 m is likely to behave as a transmission line in the PVDF or PVTrF transducer bandwidth, e.g. 2 MHz to 20 MHz). Aside from this advantage, the use of the external current source $I_{bias}$ also reduces the number of cables required. The output signal from the source follower $M_3$ inherently shares the same wire with the DC supply current. The signal and supply current can be readily separated from each other with a high-pass network $C_{ac}$ and $R_{load}$.

In order to enable a true single-wire operation, we still need to provide a bias voltage or current for the TIA. This can be achieved by utilizing DC current mirror transistors $M_2$ and $M_4$, which draw a proportion of DC current from $I_{bias}$ to the TIA while rejecting the AC currents by introducing a low-pass RC network, $R_p$ and $C_p$. In this way, the only power source for the readout circuit 60 is an external current source $I_{bias}$, which can be located at the proximal end of the catheter 81 or off-catheter. The ground reference GND of the readout circuit 60 can be provided by the shield of the micro-coaxial cable 64, which is also connected to the top electrode 65 of the PVDF or PVTrF transducer 61.

Figure 7:
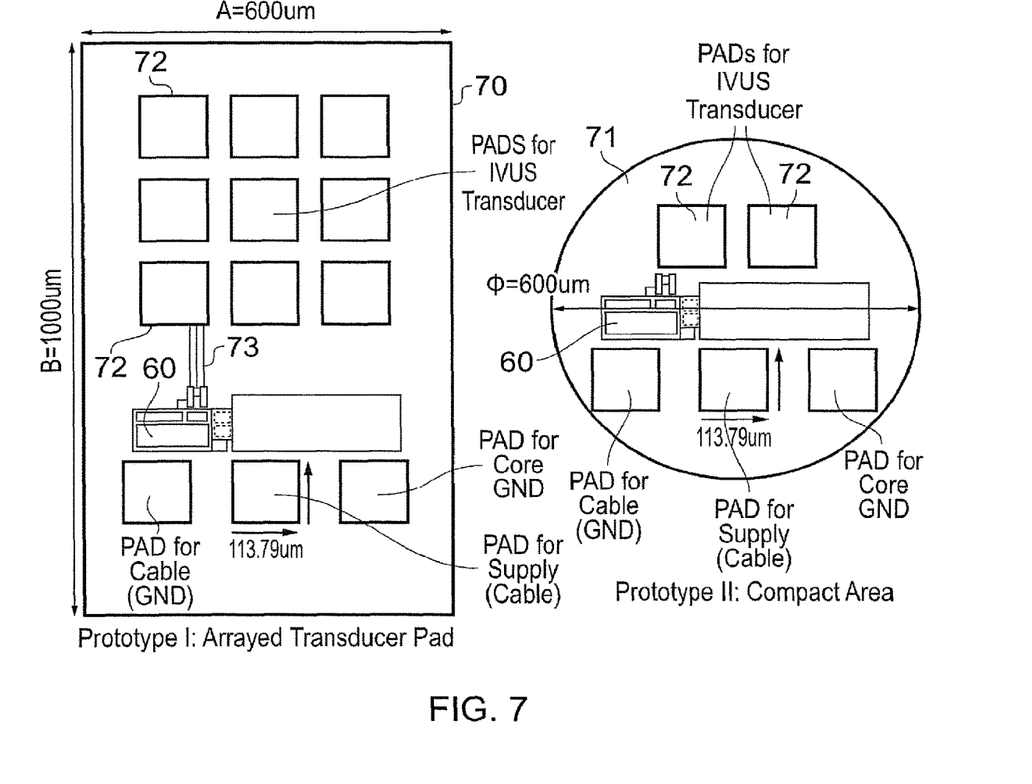
FIG. 7 shows exemplary layouts for a catheter-based photoacoustic imaging apparatus sub-assembly incorporating the readout circuit of FIG. 6.

The proposed readout circuit has been designed and fabricated in X-Fab 0.18 μm CMOS technology, with a simulated electrical performance as indicated below:
 Power Consumption: 6 mA
 Operation Bandwidth: 2 MHz-20 MHz
 Transimpedance Gain (TIA): 100 dBΩ@ 2 MHz; 80 dBΩ@ 20 MHz
 Input-Referred Noise: 5 nArms @ 2 MHz-20 MHz
 Output Impedance: ~50Ω
 Total Harmonic Distortion (THD): 0.5% @ 160 mVpp Vout FIG. 7 shows exemplary layouts for substrate 70 or 71 carrying the readout circuit 60 and the transducer 61, or both transducers 86, 87. Substrate 70 is of rectangular form with dimensions 1 mm by 0.6 mm and includes pads 72 on which the transducers may be mounted. Electrical trace 73 may serve to connect the bottom electrode 63 of the transducer 61 to the readout circuit 60.

Substrate 71 is of circular form of diameter 0.6 mm and has corresponding features.

Preferably, the readout circuit 60 is 2 mm or less in distance from the transducer 61. In the preferred embodiment, only the low frequency (e.g. PVDF) transducer needs a local readout circuit as mounted on the shared substrate 70, 71. However, depending on the transducers used, both transducers 86, 87 may use a readout circuit on the substrate 70, 71, or may share a readout circuit.

The transducers 86, 87 may comprise mechanically rotatable and/or steerable transducers within the distal portion 81c of the catheter 81, so as to allow circumferential, or part-circumferential, scanning of objects of interest around the distal portion 81c of the catheter 81. For example, the rotating transducers may enable the imaging of a circumferential section of a vessel or lumen wall.

The transducers 86, 87 may comprise electronically steerable transducers within the distal portion 81c of the catheter 81, e.g. by providing a multiple-element transducer array, to allow beam steering to scan different parts of the object of interest at or near to the distal portion of the catheter. Such beam steering techniques are known in the art.

The optical emitter 82 may also be rotatable and/or steerable in a similar manner to the transducers 86, 87, or the optical emitter may be configured to emit optical excitation signals over a wide area/full circumferential area.

The analysis module 90 and the control module 92 together effect control of the catheter-based imaging apparatus, including the timing of the optical excitation signals by the optical emitter 82; the timing of the acoustic excitation signals (e.g. pulses) from the first and/or second transducers 86, 87; control of data acquisition from the first and second transducers 86, 87; direction and/or steering of the transducers and/or optical emitter 82 if required.

Figure 9:
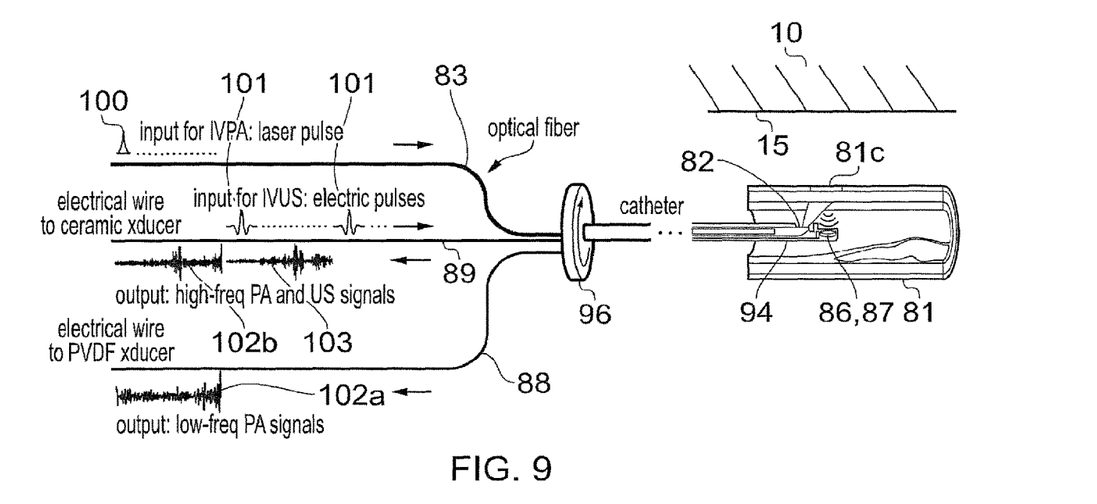
FIG. 9 shows a schematic diagram illustrating principles of operation of the catheter-based photoacoustic imaging apparatus of FIG. 8.

FIG. 9 illustrates a general principle of operation which may be adopted for a rotating catheter implementation. A mounting assembly 94 within the distal portion 81c of the catheter 81 is rotated by a suitable motor arrangement 96. The transducers 86, 87 and the optical emitter 82 are supported on the mounting assembly 94. As the mounting assembly 94 rotates, control module 92 causes light pulses 100 (optical excitation signals) and acoustic pulses 101 (acoustic excitation signals) to be transmitted towards the object of interest 10, e.g. a vessel wall 15, in an interleaved fashion.

Different pulses may be separated by at least the acoustic propagation delay time, one-way for photoacoustic response signals and two-way for pulse-echo (imaging signals). The photoacoustic response 102 to the optical excitation signals and the pulse-echo responses 103 to the insonification (acoustic excitation signals) 101 are recorded as acoustic signals as a function of time, by the low- and high-frequency transducers 86, 87. The recordings may be used to generate a colour coded amplitude signal, plotted as a function of rotation angle. The photoacoustic response may be integrated over a range of frequencies encompassed by at least the low frequency transducer 86.

In the case of the photoacoustic response 102, the signals may be received from both transducers 86 and 87, i.e. as signals 102a and 102b illustrated in FIG. 9. The signals 102a, 102b from both transducers may be processed together, in such a way as to maximize sensitivity based on the low-frequency signal, while deriving spatial resolution from the high-frequency signal. As an example, the response 102a in the low-frequency range may be applied as a multiplicative filter to the response in the high-frequency signal 102b, to achieve image detail in areas with positive signals, while suppressing noise in areas in which no lipid signal is detected. Other processing strategies are possible.

Figure 10:
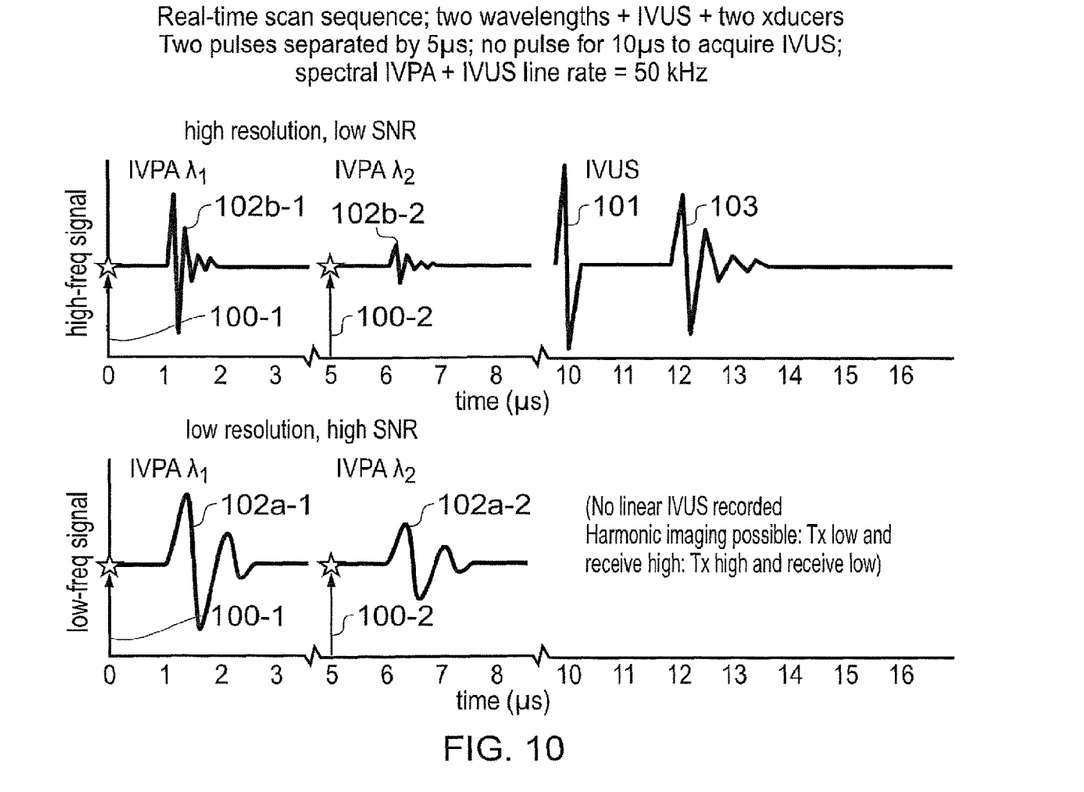
FIG. 10 shows a graphical illustration of a scan sequence according to the principles of FIG. 9.

FIG. 10 illustrates one possible arrangement of real-time scan sequences. Optical excitation pulses 100 are emitted at 0 and 5 microseconds, shown as pulses 100-1, 100-2. The photoacoustic response signals 102a detected by the low frequency transducer 86 are respectively received at 102a-1 and 102a-2. The photoacoustic response signals 102b detected by the high frequency transducer 87 are respectively received at 102b-1 and 102b-2. The response signals 102a provide low resolution but high signal to noise ratio. The response signals 102b provide high resolution but low signal to noise ratio. Subsequent to the optical excitation signals 100 and photoacoustic responses 102, at 10 microseconds an acoustic excitation signal 101 is transmitted and high resolution imaging response signal 103 is detected. For the imaging acoustic excitation signal 101 and response 103, harmonic imaging is possible, e.g. transmission 101 at a low frequency and response 103 detected at high frequency, or transmission 101 at a high frequency and response 103 detected at low frequency. Preferably, the acoustic imaging signals 101, 103 (IVUS) are temporally separated from the photoacoustic signals 100, 102 (IVPA), as exemplified in FIG. 10, but with a time period which is very small compared to the rotation speed of the transducers, such that rotational displacement of the transducers within the time period is very small or negligible. It may be possible to implement the acoustic imaging signals and the photoacoustic signals substantially simultaneously where the response signals can be separated, e.g. in the frequency domain. More generally, careful timing/synchronisation of the photoacoustic response signals 102a with the imaging response signals 101 may be used to provide high resolution positional information from the imaging signals to the photoacoustic response signals taking into account the rotation of the transducers.

A substantial number of modifications and variations may be made to the catheter-based imaging apparatus described above.

The first and second transducers 86, 87 may be replaced by a single, extended range transducer that is capable of detecting ultrasound response signals at a lower frequency at least as low as 10 MHz (e.g. the photoacoustic response signals) and at least as high as 35 MHz (e.g. the ultrasound response signals for imaging), and which is capable of emitting acoustic excitation signals at any appropriate frequency capable of causing generation, by an object of interest, of ultrasound response signals at 35 MHz, suitable for high resolution imaging. These ultrasound response signals may be backscattered/reflected ultrasound signals or could be harmonic response signals reflected or radiated by the object of interest.

It is more likely, however, that adequate performance would be better achieved with multiple transducers, each optimised for separate frequencies or frequency ranges within one of the lower frequency range and the higher frequency range, as discussed above.

The transducer or transducers may be configured to detect ultrasound response signals at one or more frequencies in the two regions 10 MHz and 35 MHz) or over one or more broad spectra at least encompassing both of the two regions. The transducer or transducers may be configured to also detect ultrasound response signals at one or more frequencies between 10 MHz and 35 MHz if responses in this region can be used to effectively to enhance imaging.

In this regard, the transducer or transducers preferably have a peak/maximum sensitivity in the photoacoustic response region (≤10 MHz) and a peak/maximum sensitivity in the ultrasound imaging response region (≥35 MHz). More preferably, the peak sensitivity in the photoacoustic response region may be in the range 2 to 4 MHz. The peak sensitivity in the ultrasound imaging response region may be in the range 35 to 45 MHz.

The transducers are preferably generally configured to have a combined sensitivity adequate or optimised for photoacoustic and ultrasonic imaging.

The catheter-based apparatus may be configured and/or optimised for the imaging of any luminal organs, lumen walls, tissue and/or other structures in or under the surfaces of those organs/lumen walls/tissue.

The optical emitter 82 may be configured to operate at one or more wavelengths. A single wavelength could be used, for example, when examining an object of interest for very specific known structures. Multiple wavelengths may be used when performing spectroscopic analysis of the structures in the object of interest.

Where multiple wavelengths are being used, the analysis module may be configured to perform an analysis of the received photoacoustic response signals generated by optical excitation signals directed to the object of interest at different optical wavelengths, to determine chemical composition of the object of interest, e.g. to determine tissue type in a lumen wall. The control unit may be configured to perform an analysis of the frequency content of the received photoacoustic response signals generated by the optical excitation signals directed to the object of interest, to determine chemical composition of the object of interest, e.g. to determine tissue type in a lumen wall.

The tissue type information may particularly determine the presence of different lipid types in and around an artery.

The chemical composition, e.g. the tissue type information may be spatially resolved.

The catheter may be fabricated as a disposable instrument, e.g. by providing only the minimum necessary elements in the catheter.

The catheter-based imaging apparatus may also be configured to provide high power optical irradiation, e.g. for irradiating tissues by continuous wave or long-pulse light to perform optical therapy on the tissues, such as ablation. The catheter-based imaging apparatus may also be configured to provide high power acoustic irradiation, e.g. long ultrasound pulses to perform acoustic therapy on the tissues, such as ablation. The catheter-based imaging apparatus may be configured with one or more ultrasound units to irradiate therapeutic substances and/or contrast agents with ultrasound pulses to push them towards the inside of a vessel wall.

The catheter-based imaging apparatus may be used in conjunction with optical or acoustic contrast dependent on an administered contrast agent in the target object of interest. The ultrasound response signals may be used to delineate a vessel wall of the object of interest.

The catheter-based imaging apparatus may be configured to generate ultrasound images using ultraharmonic and/or superharmonic response signals with or without contrast agent, e.g. by acoustically transmitting the acoustic excitation signals at low frequency and receiving the ultrasound imaging response signals at higher frequencies. The catheter-based imaging apparatus may be configured to generate ultrasound images using subharmonic response signals with or without contrast agent, e.g. by acoustically transmitting the acoustic excitation signals at high frequency and receiving the ultrasound imaging response signals at lower frequencies. A harmonics signal received from tissue of an object of interest may be used to delineate a vessel wall of the object of interest.

The lower frequency transducer 86 and the higher frequency transducer 87 may be both mounted on top of a common substrate, e.g. substrate 70 or 71. The lower frequency transducer 86 and the higher frequency transducer 87 may be mounted on the common substrate in a side-by-side or laterally adjacent configuration, or may be mounted one on top of the other in a stacked configuration on the substrate. Thus, one of the transducers 86, 87 may be mounted onto the other transducer 86, 87, which may be mounted on the common substrate, e.g. substrate 70 or 71. The second transducer may form a substrate onto which the first transducer is mounted, or vice versa. In this configuration, the underlying transducer may also be mounted onto a substrate comprising the readout circuit 60. In this manner, the first and second transducers may similarly be described as sharing a common substrate optionally with the readout circuit. The readout circuit may be positioned on the substrate adjacent to the lower frequency transducer and/or the higher frequency transducer.

In use, an intravascular ultrasound image with photoacoustic response enhancement may be produced by emitting, by the optical emitter, an optical excitation signal and, by the ultrasound transducer, an acoustic excitation signal. The optical excitation signal and the acoustic excitation signal may be emitted substantially simultaneously or at a known relative time interval, particularly if the transducers are configured for rotation in or on the catheter. The optical and acoustic excitation signals are directed to a predetermined region (target area) of the object of interest. A photoacoustic response signal and imaging response signals are received in different parts of the acoustic spectrum. Additional components of the photoacoustic response may also be received in the same part of the acoustic spectrum as the imaging response. The photoacoustic response signals are used to determine a chemical composition of the target area of the object of interest and the imaging response signals are used to generate an image of the target area of the object of interest. Repeated excitation signals are emitted directed to varying target areas, e.g. by rotation of the transducer elements and the optical emitter around the catheter axis and/or axial movement along the catheter axis. The image may be one dimensional (e.g. varying signal intensity along a circumferential line or along the catheter axis), or two dimensional (e.g. varying signal intensity in the circumferential and axial directions, or three dimensional (e.g. adding depth information indicating distance from the catheter axis).

Other embodiments are intentionally within the scope of the accompanying claims.

REFERENCES

1. MEMBERS, W. G., et al., Heart Disease and Stroke Statistics-2009 Update: A Report From the American Heart Association Statistics Committee and Stroke Statistics Subcommittee. Circulation, 2009. 119(3): p. e21-e181.
2. Naghavi, M., et al., From vulnerable plaque to vulnerable patient: a call for new definitions and risk assessment strategies: Part I. Circulation, 2003. 108(14): p. 1664-72.
3. Libby, P., Inflammation in atherosclerosis. Nature, 2002. 420(6917): p. 868-74.
4. Buja, L. M. and J. T. Willerson, Role of inflammation in coronary plaque disruption: Circulation. 1994 January; 89(1):503-5.
5. Libby, P., M. DiCarli, and R. Weissleder, The vascular biology of atherosclerosis and imaging targets. J Nucl Med, 2010. 1(51): p. 15.
6. Choudhury, R. P., V. Fuster, and Z. A. Fayad, Molecular, cellular and functional imaging of atherothrombosis. Nat Rev Drug Discov, 2004. 3(11): p. 913-25.
7. Puri, R., et al., Exploring coronary atherosclerosis with intravascular imaging. Int J Cardiol, 2013. 168(2): p. 670-9.
8. Wang, H. W., et al., Label-free bond-selective imaging by listening to vibrationally excited molecules. Phys Rev Lett, 2011. 106(23): p. 10.
9. Jansen, K., et al., Intravascular photoacoustic imaging of human coronary atherosclerosis. Opt Lett, 2011. 36(5): p. 597-9.
10. Wang, B., et al., Intravascular photoacoustic imaging of lipid in atherosclerotic plaques in the presence of luminal blood. Opt Lett, 2012. 37(7): p. 1244-6.
11. Wang, P., J. R. Rajian, and J. X. Cheng, Spectroscopic Imaging of Deep Tissue through Photoacoustic Detection of Molecular Vibration. J Phys Chem Lett, 2013. 4(13): p. 2177-2185.
12. Ma, J., et al., A preliminary engineering design of intravascular dual-frequency transducers for contrast-enhanced acoustic angiography and molecular imaging. IEEE Trans Ultrason Ferroelectr Freq Control, 2014. 61(5): p. 870-80.
13. Jansen, K., G. van Soest, and A. F. W. van der Steen, Intravascular Photoacoustic Imaging: A New Tool for Vulnerable Plaque Identification. Ultrasound in Medicine & Biology, 2014. 40(6): p. 1037-1048.
14. Paul, C. B. and C. Ben, Modeling Photoacoustic Propagation in Tissue Using k-Space Techniques, in Photoacoustic Imaging and Spectroscopy 2009, CRC Press. p. 25-34.
15. Jansen, K., et al., Lipid detection in atherosclerotic human coronaries by spectroscopic intravascular photoacoustic imaging. Optics Express, 2013. 21(18): p. 21472-21484.
16. Diebold, G. J., M. I. Khan, and S. M. Park, Photoacoustic "signatures" of particulate matter: optical production of acoustic monopole radiation. Science, 1990. 250(4977): p. 101-4.
17. Hysi, E., D. Dopsa, and M. C. Kolios. Photoacoustic radio-frequency spectroscopy (PA-RFS): A technique for monitoring absorber size and concentration. 2013.
18. Kumon, R. E., C. X. Deng, and X. Wang, Frequency-domain analysis of photoacoustic imaging data from prostate adenocarcinoma tumors in a murine model. Ultrasound Med Biol, 2011. 37(5): p. 834-9.
19. Gertsch, A. G., et al. Toward characterizing the size of microscopic optical absorbers using optoacoustic emission spectroscopy. 2010.

The invention claimed is:

1. A catheter-based imaging apparatus comprising:
a catheter having a proximal end and a distal end;
an optical emitter configured to emit optical excitation signals from a distal portion of the catheter;
a first transducer and a second transducer, wherein:
  the first transducer has a peak detection sensitivity in a lower frequency range of a first frequency to a second frequency;
  the second transducer has a peak detection sensitivity in a higher frequency range of a third frequency to a fourth frequency, the third frequency being no less than the second frequency, and
  the catheter-based imaging apparatus is configured for:
  (a) transmission of acoustic excitation signals from the distal portion of the catheter with the second transducer;
  (b) detection of a photoacoustic response signal with the first transducer, the photoacoustic response signals being from an object of interest at or near to the distal portion of the catheter and excited by the optical excitation signals and
  (c) detection of imaging signals with the second transducer, the imaging signals comprising reflections of the acoustic excitation signals from the object of interest wherein the first transducer is configured to be operable at a frequency range which encompasses a lower receive frequency at least as low as 10 MHz and the second transducer is configured to be operable at a frequency range that encompasses a higher receive frequency at least as high as 35 MHz.

2. The catheter-based imaging apparatus of claim 1, wherein the first transducer comprises a piezoelectric polymer transducer or a piezoelectric composite transducer and the second transducer comprises a piezoelectric ceramic transducer or a piezoelectric composite transducer.

3. The catheter-based imaging apparatus of claim 1, wherein the first transducer and the second transducer are laterally adjacent to each other.

4. The catheter-based imaging apparatus of claim 3, wherein the first transducer is located distal to the second transducer.

5. The catheter-based imaging apparatus of claim 3, wherein the first transducer is located proximal to the second transducer.

6. The catheter-based imaging apparatus of claim 3, further comprising charge readout circuit, wherein
the first transducer comprises a PVDF transducer, the PVDF transducer and the charge readout circuit being disposed on a common substrate, and
the second transducer comprises a piezoelectric ceramic transducer or a piezoelectric composite transducer.

7. The catheter-based imaging apparatus of claim 1, wherein the first transducer and the second transducer are in a side-by-side configuration.

8. The catheter-based imaging apparatus of claim 1, wherein the first transducer and the second transducer are in a back-to-back configuration.

9. The catheter-based imaging apparatus of claim 7, further comprising charge readout circuit, wherein
the first transducer comprises a PVDF transducer, the PVDF transducer and the charge readout circuit being disposed on a common substrate, and
the second transducer comprises a piezoelectric ceramic transducer or a piezoelectric composite transducer.

10. The catheter-based imaging apparatus of claim 8, further comprising charge readout circuit, wherein
the first transducer comprises a PVDF transducer, the PVDF transducer and the charge readout circuit being disposed on a common substrate, and
the second transducer comprises a piezoelectric ceramic transducer or a piezoelectric composite transducer.

11. The catheter-based imaging apparatus of claim 4, further comprising charge readout circuit, wherein
the first transducer comprises a PVDF transducer, the PVDF transducer and the charge readout circuit being disposed on a common substrate, and
the second transducer comprises a piezoelectric ceramic transducer or a piezoelectric composite transducer.

12. The catheter-based imaging apparatus of claim 5, further comprising charge readout circuit, wherein
the first transducer comprises a PVDF transducer, the PVDF transducer and the charge readout circuit being disposed on a common substrate, and
the second transducer comprises a piezoelectric ceramic transducer or a piezoelectric composite transducer.

* * * * *